(12) United States Patent
Sall

(10) Patent No.: US 10,500,353 B2
(45) Date of Patent: Dec. 10, 2019

(54) MEDICAMENT DELIVERY DEVICE

(71) Applicant: Carebay Europe Ltd., Sliema (MT)

(72) Inventor: Daniel Sall, Segel-torp (SE)

(73) Assignee: SHL Medical, AG, Zug (CH)

( * ) Notice: Subject to any disclaimer, the term of this patent is extended or adjusted under 35 U.S.C. 154(b) by 0 days.

(21) Appl. No.: 15/515,094

(22) PCT Filed: Sep. 30, 2015

(86) PCT No.: PCT/EP2015/072648
§ 371 (c)(1),
(2) Date: Mar. 28, 2017

(87) PCT Pub. No.: WO2016/055334
PCT Pub. Date: Apr. 14, 2016

(65) Prior Publication Data
US 2018/0228984 A1    Aug. 16, 2018

(30) Foreign Application Priority Data

Oct. 8, 2014  (SE) ...................................... 1451199

(51) Int. Cl.
| | |
|---|---|
| *A61M 5/00* | (2006.01) |
| *A61M 5/50* | (2006.01) |
| *A61M 5/32* | (2006.01) |
| *A61M 5/28* | (2006.01) |

(52) U.S. Cl.
CPC ........ *A61M 5/5086* (2013.01); *A61M 5/3204* (2013.01); *A61M 5/28* (2013.01); *A61M 5/3213* (2013.01); *A61M 2005/3247* (2013.01)

(58) Field of Classification Search
CPC ............ A61M 2005/3247; A61M 5/28; A61M 5/3204; A61M 5/3213; A61M 5/5086
See application file for complete search history.

(56) References Cited

U.S. PATENT DOCUMENTS

| | | | |
|---|---|---|---|
| 2008/0228147 A1* | 9/2008 | David-Hegerich ... | A61M 5/326 604/198 |
| 2010/0094214 A1 | 4/2010 | Abry et al. | |

FOREIGN PATENT DOCUMENTS

| | | |
|---|---|---|
| EP | 1970086 A2 | 9/2008 |
| WO | 2009040603 A1 | 4/2009 |

* cited by examiner

*Primary Examiner* — Rebecca E Eisenberg
(74) *Attorney, Agent, or Firm* — McDonnell Boehnen Hulbert & Berghoff LLP

(57) ABSTRACT

The present disclosure relates to a medicament delivery device for injection of a medicament. The medicament delivery device comprises a housing (3) arranged to receive a medicament delivery member, a medicament delivery member cover (7) received by the housing (3), which medicament delivery member cover (7) has a cap-fitting portion (7a), wherein the medicament delivery member cover (1) is moveable relative to the housing (3) from an extended position in which the cap-fitting portion (7a) extends from the housing (3), to a retracted position in which the medicament delivery member cover (7) is biased towards the extended position, and a cap (11) arranged to receive the cap-fitting portion (7a), wherein the medicament delivery member cover (7) and the cap (1) comprise a tamper evidence mechanism which is activated by removal of the cap (11) from the cap-fitting portion (7a).

18 Claims, 4 Drawing Sheets

MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2015/072648 filed Sep. 30, 2015, which claims priority to Swedish Patent Application No. 1451199-2 filed Oct. 8, 2014. The entire disclosure contents of these applications are herewith incorporated by reference into the present application.

TECHNICAL FIELD

The present disclosure generally relates to a medical device and in particular to a medicament delivery device for administration of a medicament to a patient.

BACKGROUND

A parameter which may be taken into account when designing medicament delivery devices is that of enabling patients to identify medicament delivery to devices which have been tampered with prior to use.

An example of a device for automatic injection which provides tampering protection is disclosed in WO2009/040603 A1. The device comprises a needle and a needle shield for protecting the needle. The device further comprises a housing arranged to receive a container, and a deshielder for removing the needle shield. The deshielder is coupled to the needle shield and mounted to the housing in a separable manner, through breakable or snap-fit means. The deshielder comprises tamper evidence means that are activated by the removal of at least one part of the deshielder. The removal of the deshielder from the housing prevents the deshielder from being put back on the housing.

SUMMARY

A general object of the present disclosure is to provide a medicament delivery device which is able to indicate if it has been tampered with.

There is hence provided a medicament delivery device for injection of a medicament, comprising a housing arranged to receive a medicament delivery member, a medicament delivery member cover received by the housing, which medicament delivery member cover has a cap-fitting portion, wherein the medicament delivery member cover is moveable relative to the housing from an extended position in which the cap-fitting portion extends from the housing, to a retracted position in which the medicament delivery member cover is biased towards the extended position, and a cap arranged to receive the cap-fitting portion, wherein the medicament delivery member cover and the cap comprise a tamper evidence mechanism which is activated by removal of the cap from the cap-fitting portion.

By means of the this design, evidence of tampering of the medicament delivery device prior to medicament administration may be provided, in particular for medicament delivery devices which comprise a medicament delivery member cover arranged in the housing. A medicament delivery to device of this type comprises a medicament delivery member cover which is movable relative to the housing, and which comprises a cap-fitting portion which extends from the housing in the extended position and is received by the housing in the retracted position, thus providing additional protection of the delivery member until the medicament administration procedure.

The tamper evidence mechanism enables removal of the cap from the cap-fitting portion, but does not allow the cap to be fitted properly on the cap-fitting portion once the cap has been removed. Tampering of the medicament delivery device can thereby be identified.

The words "distal end" and "proximal end" may be used in conjunction with any of the components of the medicament delivery device. In each case, "proximal end" refers to that end of the component which is the end of component in the direction in which a medicament delivery member arranged in the housing points, and "distal end" refers to the opposite end.

According to one embodiment, the tamper evidence mechanism comprises a groove and a first shoulder, which first shoulder is arranged in the groove prior to removal of the cap.

According to one embodiment the tamper evidence mechanism comprises a flexible tongue, wherein the first shoulder defines an end portion of the flexible tongue. The first shoulder may thereby be bent radially which enables disengagement of the first shoulder from the groove when the cap is removed from the cap-fitting portion of the medicament delivery member cover.

According to one embodiment the first shoulder gradually increases in radial dimension along the axial direction, in the direction which enables release of the first shoulder from the groove by means of axial motion. The first shoulder may thereby be disengaged from the groove when the cap is removed from the cap-fitting portion.

According to one embodiment the groove is defined by a surface which along the axial direction gradually increases in depth from its edge towards the midpoint of the groove. Disengagement of the first shoulder may thereby be facilitated when removing the cap from the cap-fitting portion.

According to one embodiment the tamper evidence mechanism comprises a second shoulder arranged adjacent to the groove in the axial direction, wherein the second shoulder has a first shoulder abutment surface arranged in an opposite direction relative to a second shoulder abutment surface of the first shoulder when the cap-fitting portion is received by the cap. The second shoulder is hence arranged in the downstream direction of the groove, with the downstream direction being defined as the direction in which the first shoulder moves relative to the cap when the cap is removed from the cap-fitting portion. More particularly, when the cap is proximally moved relative to the medicament delivery member cover. The first shoulder abutment surface and the second shoulder abutment surface will thereby abut or bear against each other when the cap is returned onto the medicament delivery member cover after having been removed, preventing the first shoulder from being received in the groove.

According to one embodiment the second shoulder increases gradually in radial dimension in the opposite direction relative to the direction along which the first shoulder gradually increases in radial dimension. More particularly, the second shoulder increases gradually in radial dimension in the proximal direction and the first shoulder gradually increases in radial dimension in the distal direction.

According to one embodiment the groove is provided on an internal surface of the cap and the first shoulder is arranged on an external surface of the medicament delivery member cover.

According to one embodiment the groove extends along the inner periphery of the cap.

According to one embodiment the housing has a guide structure extending axially along the internal surface of the housing, wherein the guide structure is arranged to cooperate with that part of the tamper evidence mechanism which is arranged on the medicament delivery member cover. The guide structure thus acts as a guide for the medicament delivery member cover when it is slid axially relative to the housing. The risk of rotational motion of the housing relative to the medicament delivery member cover during relative axial movement between the housing and the medicament delivery member cover may thereby be eliminated or at least reduced. Rotational motion between these components may damage the medicament delivery member.

The tamper evidence mechanism according to this embodiment hence has dual functions, namely to act as a tamper evidence mechanism, and for preventing rotational motion between the housing and the medicament delivery member cover.

According to one embodiment the guide structure comprises a groove arranged to receive the first shoulder of the tamper evidence mechanism.

According to one embodiment the guide structure comprises a rib, wherein the first shoulder of the tamper evidence mechanism is arranged to receive the rib.

According to one embodiment the groove and the first shoulder define a snap fit mechanism.

One embodiment comprises a medicament delivery member deshielder which has a proximal end flange, wherein the cap is arranged to receive the medicament delivery member deshielder along its central axis, which cap has an inner flange arranged to cooperate with the proximal end flange of the medicament delivery member deshielder.

According to one embodiment the cap has a stop member, wherein the stop member and the inner flange defines a play for the proximal end flange of the medicament delivery member deshielder, wherein the axial distance between the stop member and the inner flange is at least as large as the axial distance between the first shoulder abutment surface and a midpoint of the groove. The total force at any instant in time when removing the cap will therefore not be greater than the largest force necessary to 1) disengage the first shoulder from the groove when removing the cap from the medicament delivery member cover, and 2) to remove the medicament delivery member deshielder from a medicament delivery member when removing the cap from the medicament delivery member cover. The two forces will in particular not be added to each other, because the play allows for movement of the medicament delivery member deshielder from the stop member to the inner flange when the cap is moved a first distance axially in a first phase of the procedure of removing the cap. It is during this first distance that the first shoulder is disengaged from the groove. When the first shoulder has been released from the groove, the procedure reaches a second phase when the proximal end flange engages the inner flange of the cap. During the second phase, the medicament delivery member deshielder is moved concurrently with the cap as the cap is removed from the cap-fitting portion and from the housing. Due to the construction, the two forces mentioned above hence act in a serial manner. This may in particular be relevant for patients that have medical disorders, for example rheumatism, which may reduce the strength of the patient.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

Figure 1:
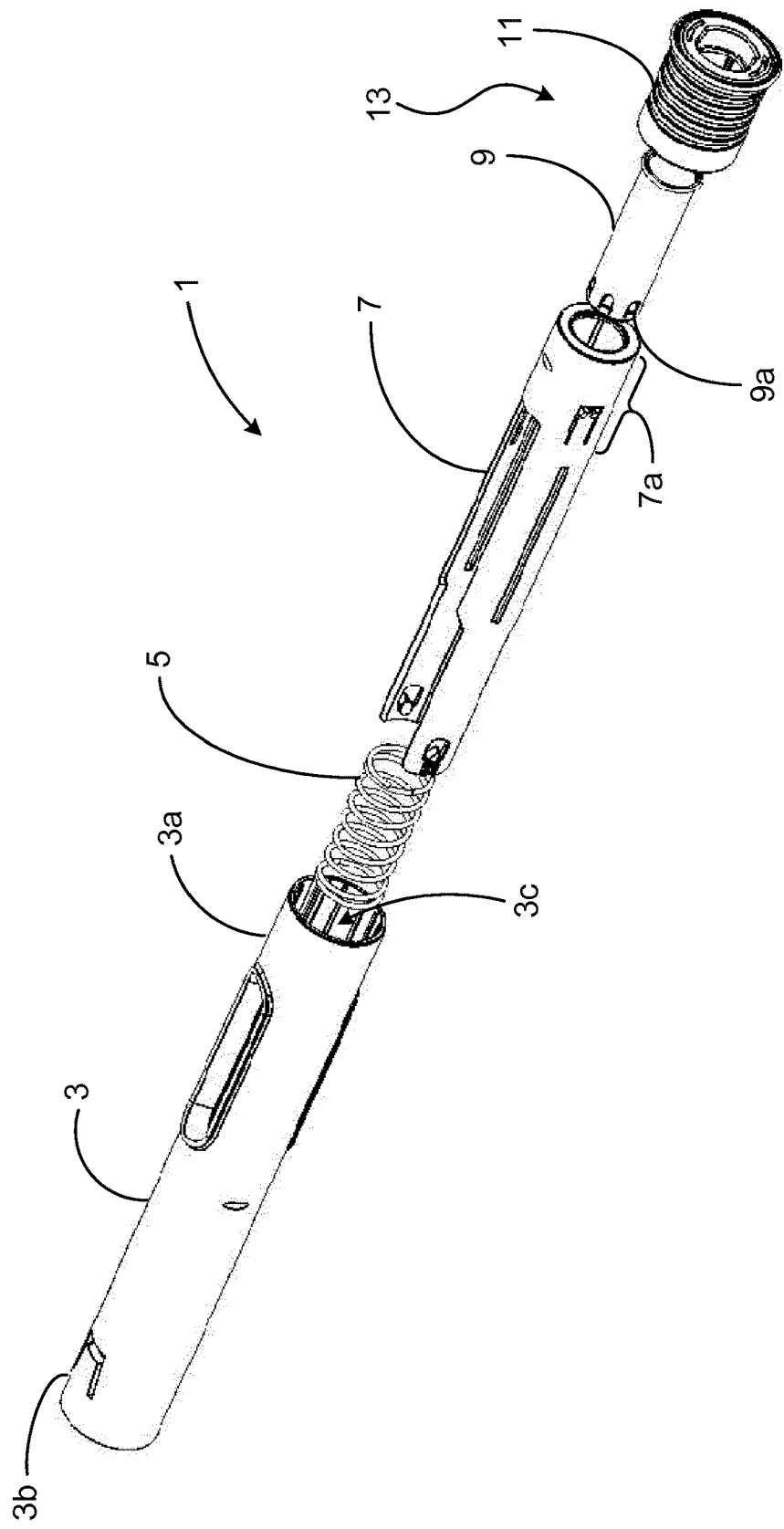
FIG. 1 is an exploded view of an example of a medicament delivery device.

FIG. 1 depicts an exploded view of an example of a medicament delivery device 1. The medicament delivery device 1 is arranged to receive a delivery member, such as a needle or a nozzle, and an associated medicament container containing a drug for administration thereof to a patient.

The medicament delivery device 1 comprises a housing 3, a biasing member 5, e.g. an energy accumulation device such as a spring, a medicament delivery member cover 7, a medicament delivery member deshielder 9 and a cap 11. The cap 11 and the medicament delivery member deshielder 9 form a cap assembly 13.

The housing 3 has a proximal end 3a and a distal end 3b. The housing 3 is arranged to receive the medicament delivery member cover 7. The medicament delivery member cover 7 may hence be coaxially arranged in the housing 3.

The medicament delivery member cover 7 has a cap-fitting portion 7a, which is defined by the proximal end portion of the medicament delivery member cover 7. The housing 3 has an opening 3c at its proximal end 3a from which the cap-fitting portion 7a can extend when the medicament delivery member cover 7 is arranged in the housing 3.

The medicament delivery member cover 7 is movable relative to the housing 3 when arranged in the housing 3. The medicament delivery member cover 7 is movable between an extended position in which the cap-fitting portion 7a extends from the housing 3 and a retracted position in which the medicament delivery member cover 7 is substantially inserted into the housing. In the retracted position, the medicament delivery member is exposed, enabling administration of a medicament contained in a medicament container.

The biasing member 5 may in a typical example be arranged in the opening 3c, received also by the medicament delivery member cover 7.

The cap-fitting portion 7a of the medicament delivery member cover 7 is arranged to be received coaxially by the cap 11. Access to a delivery member, such a needle or a nozzle, which together with a medicament container can be contained inside the housing 3, can thereby be restricted until the cap 11 is removed from the medicament delivery member cover 7.

Figure 5A:
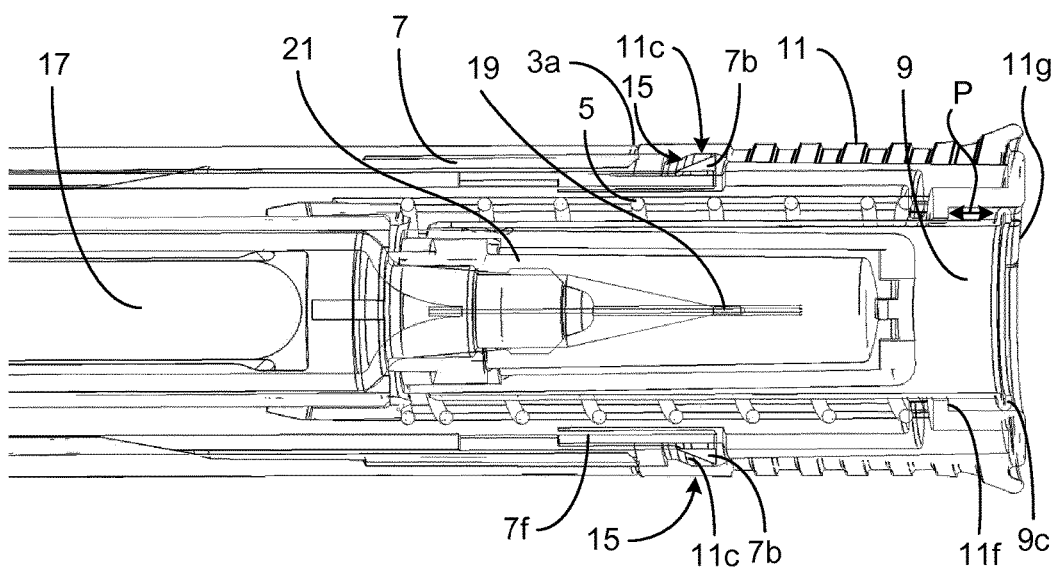
FIGS. 5a-d shows the medicament delivery device in FIG. 1 in use.

The cap 11 and the medicament delivery member cover 7 have a tamper evidence mechanism 15, as shown in FIG. 5a. The tamper evidence mechanism 15 is activated by removal of the cap 11 from the medicament delivery member cover 7. The tamper evidence mechanism 15 permits removal of the cap 11 from the medicament delivery member cover 7 and prevents engagement of the cap 11 and the medicament delivery member cover 7 once the cap 11 has been removed. According to the example shown in FIG. 5a, the tamper evidence mechanism 15 comprises a groove 11c and a first shoulder 7b which engage with each other prior to removal of the cap 11 from to the medicament delivery member cover 7.

The cap 11 is arranged to receive a portion of the medicament delivery member deshielder 9. In particular, the cap 11 and the medicament delivery member deshielder 9 are arranged to engage with each other such that when the cap 11 is removed from the cap-fitting portion 7a, the medicament delivery member deshielder 9 is removed simultaneously with the cap 11.

The medicament delivery member deshielder 9 may comprise engagement members 9a arranged to engage a medicament delivery member shield, not shown, which thereby can be removed when the cap 11 is pulled off the medicament delivery member cover 7.

Figure 2:
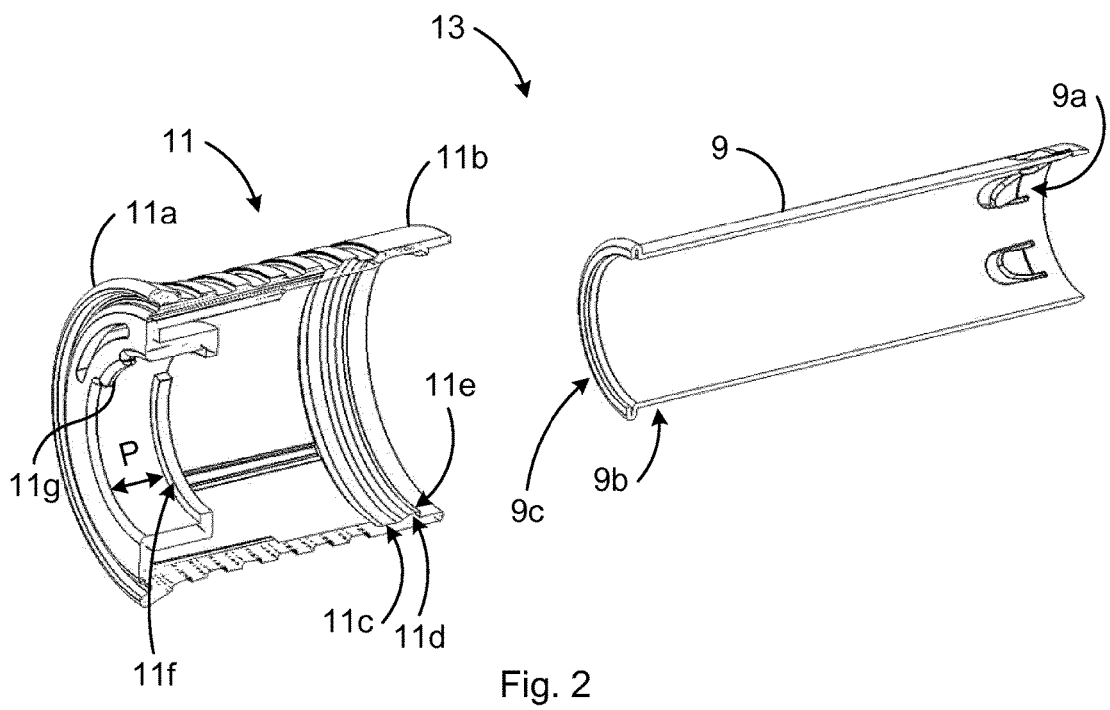
FIG. 2 shows a longitudinal section of a cap assembly of the medicament delivery device in FIG. 1.

FIG. 2 shows a longitudinal section of the cap assembly 13. The medicament delivery member deshielder 9 is generally tubular and has a proximal end 9b and a proximal end flange 9c. The proximal end flange 9c extends radially outwards from the medicament delivery member deshielder 9. The proximal end flange 9c may for example extend along a majority of the outer periphery, or along the outer periphery, of the medicament delivery member deshielder 9.

The cap 11 is generally tubular and has a proximal end 11a and a distal end 11b. According to the example in FIG. 2, the cap 11 has a groove 11c which forms part of the tamper evidence mechanism 15 shown in FIG. 5a. The groove 11c is provided on the internal surface of the cap 11. The groove 11c may extend along the or essentially the periphery of the cap 11. The groove 11c has a sloping surface in the axial direction from its distal edge towards its midpoint. The depth of the groove 11 hence gradually increases from the distal edge towards the midpoint in the proximal direction. The groove 11c is arranged in proximity to the distal end 11b. In particular, the groove 11c is arranged closer to the distal end 11b than to the proximal end 11a.

According to the example shown in FIG. 2, the cap 11 has a shoulder 11d which also forms part of the tampering evidence mechanism 15. This shoulder 11d will in the following be referred to as "second shoulder", the first shoulder 7b of the tampering evidence mechanism 15 being that of the medicament delivery member cover 7. The second shoulder 11d is arranged adjacent to the groove 11c, in the axial direction towards the distal end 11b of the cap 11. The second shoulder 11d defines a first, distally facing, shoulder abutment surface 11e. The first shoulder abutment surface 11e defines a transversal plane, intersecting the central axis if the cap 11. The first shoulder abutment surface 11e may according to one variation define both a transversal and a radial plane, i.e. a cross-sectional plane.

The cap 11 further comprises an inner flange 11f which extends radially inwards. The inner flange 11f extends along an inner periphery of the cap 11. The inner flange 11f is arranged in proximity with the proximal end 11a of the cap 11. In particular, the inner flange 11f is arranged closer to the proximal end 11a than to the distal end 11b. The inner flange 11f is arranged to cooperate with the proximal end flange 9c of the medicament delivery member deshielder 9.

The cap 11 comprises a stop member 11g which extends radially inwards. The stop member 11g is arranged closer to the proximal end 11a than the inner flange 11f is. A play P is defined between the stop member 11g and the inner flange 11f. The proximal end flange 9c is arranged to be movable in this play P between the inner flange 11f and the stop member 11g when the medicament delivery member deshielder 9 has been assembled with the cap 11. The cap 11 and the medicament delivery member deshielder 9 are hence movable relative to each other in an assembled state.

Figure 3:
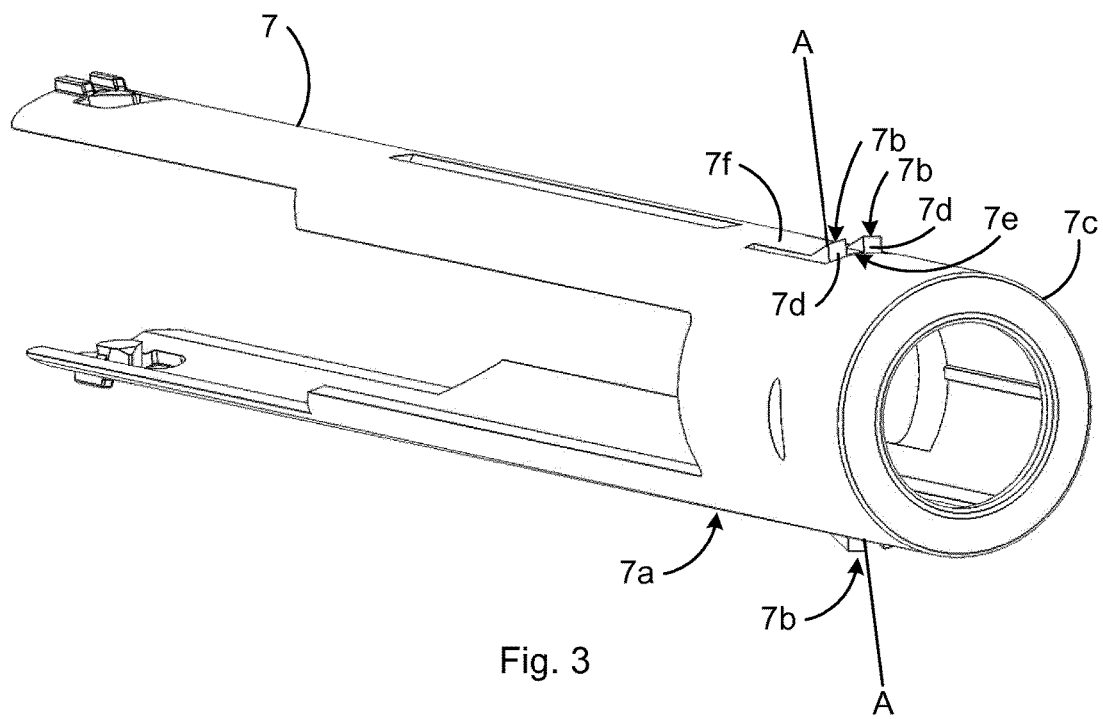
FIG. 3 shows a perspective view of a medicament delivery member cover of the medicament delivery device in FIG. 1.

FIG. 3 shows the medicament delivery member cover 7. The medicament delivery member cover 7 comprises part of the tamper evidence mechanism 15 shown in FIG. 5a. In particular, the medicament delivery member cover 7 has a first shoulder 7b arranged to engage the groove 11b of the cap 11 when the cap-fitting portion 5a is initially received by the cap 11. The first shoulder 7b increases in radial dimension gradually, in the axial direction towards the proximal end 7c of the medicament delivery member cover 7. The first shoulder 7b may for example be wedge-shaped. The first shoulder 7b has a second, proximally facing, shoulder abutment surface 7d which defines a transversal plane, intersecting the central axis of the medicament delivery member cover 7. The second shoulder abutment surface 7d may according to one variation define both a transversal and a radial plane, i.e. a cross-sectional plane.

According to one variation, the first shoulder 7b may comprise a groove 7e extending in the axial direction. According to this variation, the groove 7e splits the first shoulder 7b into two portions.

According to one variation, the medicament delivery member cover 7 comprises a flexible tongue 7f. The flexible tongue 7f may for example have one end which is integral with the medicament delivery member cover 7, while the remaining sides are free, enabling radial bending of the flexible tongue 7f. The first shoulder 7b is arranged at the free end portion of the flexible tongue 7f, to enable radial displacement of the first shoulder 7b.

According to one variation, the medicament delivery member cover 7 may comprise several sets of second shoulders 7b, for example spaced apart at 180°, or less, along the external surface of the medicament delivery member cover 7.

The groove 11c is preferably arranged at such a distance from the distal end 11b of the cap 11 that the distal end 11b essentially bears against or abuts the proximal end 3a of the housing when the cap 11 is arranged around the cap-fitting portion 7a and the first shoulder 7b engages the groove 11c. The cap 11 is hence essentially fixed relative to the housing 3 in this initial state of the medicament delivery device 1.

Figure 4:
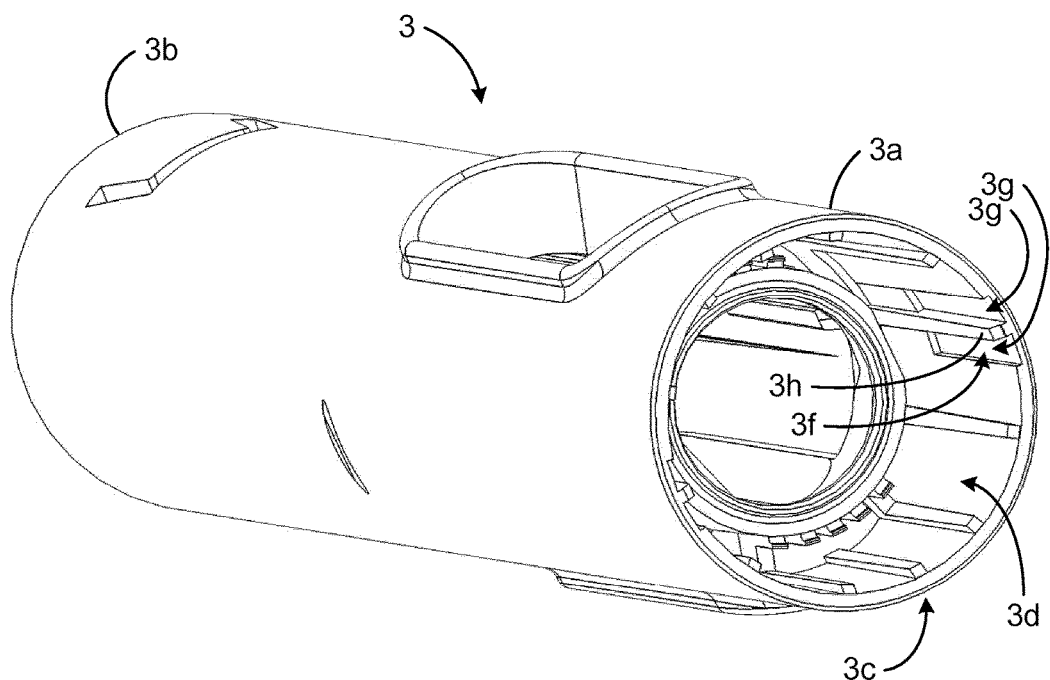
FIG. 4 is a perspective view of a housing of the medicament delivery device in FIG. 1.

FIG. 4 shows a perspective view of the housing 3, in particular seen from the proximal end. The inner surface 3d at the proximal end 3a of the housing 3 has a guide structure 3f. The guide structure 3f is arranged to cooperate with that part of the tamper evidence mechanism 15 which belongs to the medicament delivery member cover 7. According to the present example, the guide structure 3*f* is arranged to cooperate with the first shoulder 7*b*.

The guide structure 3*f* comprises two parallel grooves 3*g* and a rib 3*h* arranged between the grooves 3*g* and extending along the two grooves 3*g*. The grooves 3*g* are arranged to receive the two portions of the first shoulder 7*b* when the medicament delivery member cover 7 is moved towards its retracted position. The rib 3*h* is arranged to be received between the two portions of the first shoulder 7*b*, into groove 7*e* of the medicament delivery member cover 7.

The guide structure 3*f* defines a guide for the first shoulder 7*b* such that when the medicament delivery member cover 7 is moved from the extended position to the retracted position, rotational motion of the medicament delivery member cover 7 relative to the housing 3 is restricted. The guide structure 3*f* hence permits axial motion of the medicament delivery member cover 7 and prevents rotational motion thereof.

The operation of the medicament delivery device 1 will now be described with reference to FIGS. 5*a*-*d*. FIG. 5*a* depicts a longitudinal section of a proximal portion of the medicament delivery device 1. The section is taken so that it corresponds to section A-A of the medicament delivery member cover 7 in FIG. 3. In the exemplified figure, the medicament delivery device 1 is shown containing a medicament container 17, a medicament delivery member 19 here exemplified by a needle, and a medicament delivery member shield 21 protecting the delivery member 19.

In FIG. 5*a* the medicament delivery member cover 7 is received by the cap 11. The cap 11 is thus arranged around the cap-fitting portion 7*a* of the medicament delivery member cover 7. The fitting of the cap 11 may for example be performed when assembling the medicament delivery device 1.

The medicament delivery member cover 7 is shown in the extended position. In the extended position the cap-fitting portion 7*a* protrudes from the housing 3 and the first shoulder 7*b* is distanced, in the axial direction, from to the proximal end 3*a* of the housing 3.

The first shoulder 7*b* is arranged in the groove 11*c* of the cap 11. The first shoulder 7*b* and the groove 11*c* form a snap-fit mechanism which enables disengagement of the first shoulder 7*b* from the groove 11*c*. Due to the gradual increase in radial dimension of the first shoulder 7*b* and due to the corresponding gradual decrease in the depth of the groove 11*c*, the first shoulder 7*b* is able to disengage from the groove 11*c* when the cap 11 is pulled away from the housing 3. The disengagement is furthermore obtainable because of the flexibility of the flexible tongue 7*f*, which is able to bend radially inwardly when the cap 11 is pulled away from the housing 3 and the first shoulder 7*b* slides out from the groove 11*c*.

In the retracted position of the medicament delivery member cover 7 shown in FIG. 5*a*, the proximal end flange 9*c* of the medicament delivery member deshielder 9 bears against or abuts the stop member 11*g*. The cap 11 is hence proximally movable a distance essentially corresponding to the play P during which the medicament delivery member deshielder 9 remains stationary relative to the housing 3. When the cap it has been pulled a distance corresponding to the play P, the inner flange 11*f* engages the proximal end flange 9*c* and as a result the medicament delivery member deshielder 9 follows the motion of the cap 11 from this point. The force required to disengage the first shoulder 7*b* from the groove 11*c* does hence not add to the force required to pull off the medicament delivery member shield 21 because the force to disengage the first shoulder 7*b* and the force to remove the medicament delivery member shield 21 act in a serial manner; first the first shoulder disengagement force and then the medicament delivery member shield removal force.

Thus, according to one variation, the axial distance between the stop member 11*g* and the inner flange 11*f* is at least as large as the axial distance between the first shoulder abutment surface lie and a midpoint of the groove 11*c*. Thus, when the cap 11 is initially moved during cap removal, the disengagement of the free shoulder 7*b* and the groove 11*c* may be performed without engagement of the inner flange 11*f* of the cap 11 and the proximal end flange 9*c* of the medicament delivery member deshielder 9. As previously noted, engagement of these components only occur when the tampering evidence mechanism 15 has been activated by disengagement of the first shoulder 7*b* and the groove 11*c*.

Figure 5B:
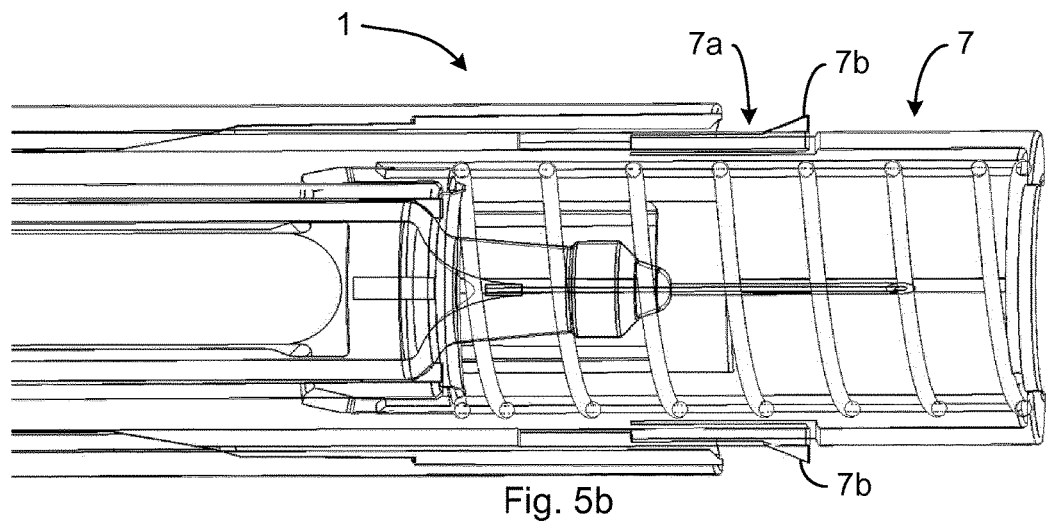

In FIG. 5*b* the medicament delivery device 1 is shown when the cap 11 has been removed from the cap-fitting portion 7*a*, and the medicament delivery member shield 21 has been pulled off by means of the medicament delivery member deshielder 9 simultaneously with the cap 11. The medicament delivery device 1 is in this state ready for medicament administration and the proximal end of the medicament delivery member cover 7 may be placed onto the surface of an object that is to be the subject of medicament administration.

Figure 5C:
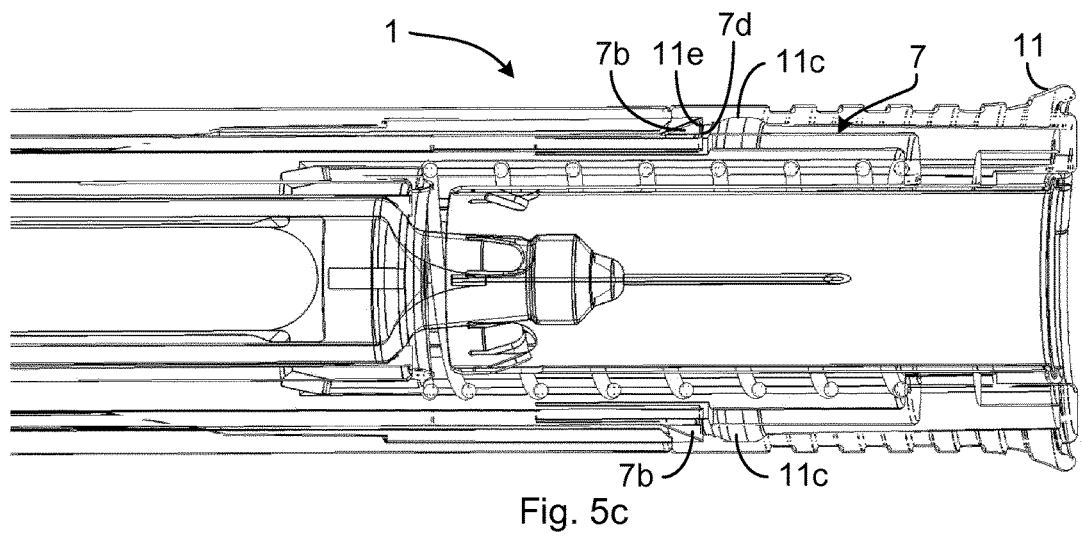

FIG. 5*c* shows when the cap 11 has been returned to the cap-fitting portion 7*a* of the medicament delivery member cover 7. In FIG. 5*c*, the cap 11 is pushed maximally onto the medicament delivery member cover 7, which then moves towards its retracted position.

When the cap 11 is pushed onto the medicament delivery member cover 7, the first shoulder abutment surface 11*e* of the cap 11 abuts or bears against the second shoulder abutment surface 7*d* of the medicament delivery member cover 7. Due to the two surfaces being essentially parallel and essentially parallel to a cross-sectional plane, the first shoulder 7*b* is not permitted to slide into the groove 11*c* as the flexible tongue 7*f* in this case will not bend radially inwards.

Figure 5D:
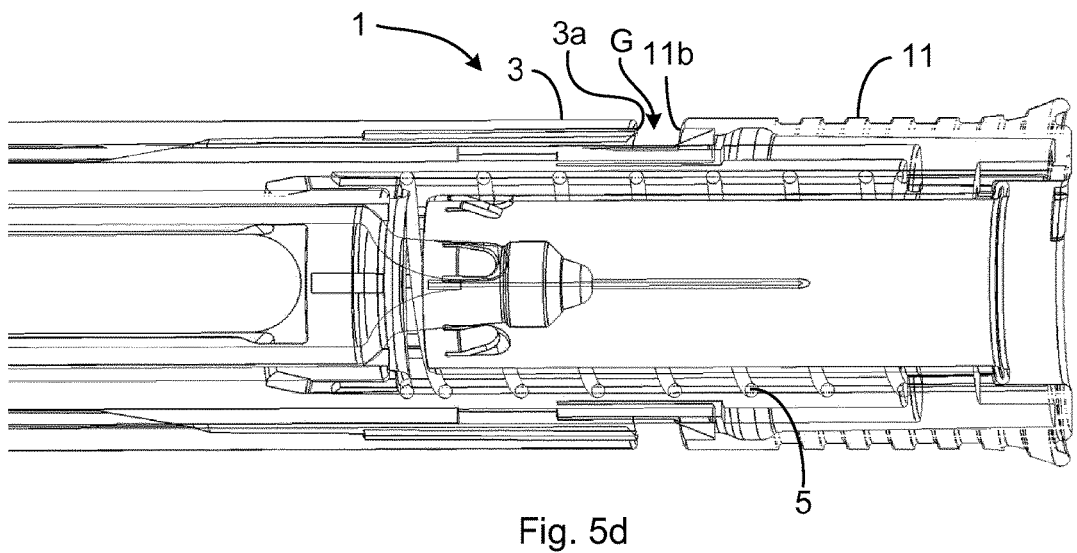

In the illustration in FIG. 5*d* the axial force present in FIG. 5*c* is no longer applied to the cap 11. The biasing member 5 hence sets the medicament delivery member cover 7 into its extended position. As a result, a gap G is formed between the proximal end 3*a* of the housing 3 and the distal end 11*b* of the cap 11. Thus, when the cap 11 has once been removed from the medicament delivery member cover 7, this may be easily identified both visually due to the gap G and tactilely because the cap 11 is movable towards the housing 3. Any tampering of the medicament delivery device 1 may thus in a simple manner be identified.

The length of the flexible tongue and the radial dimension of the first shoulder determine the pulling force that is necessary to disengage the first shoulder from the groove. The shorter the flexible tongue and/or the larger the radial dimension of the first shoulder, the more force will be necessary to remove the cap 11. These two parameters may hence be taken into account when designing the medicament delivery device for different patient groups.

The medicament delivery device may be a disposable medicament delivery device or a medicament delivery device of the type which may be reused multiple times.

The medicament delivery device may for example be an injector, an eye dispenser or an inhaler. The medicament delivery member which may be utilised with the medicament delivery device 1 may for example be a needle or a nozzle. The medicament delivery member cover 7 may thus for example be a needle cover or a nozzle cover. The medicament delivery member deshielder 9 may for example be a rigid needle shield or flexible needle shield, in the event that the medicament delivery member is a needle.

The inventive concept has mainly been described above with reference to a few examples. However, as is readily appreciated by a person skilled in the art, other embodiments than the ones disclosed above are equally possible within the scope of the inventive concept, as defined by the appended claims. For example, the first shoulder may be arranged on an internal surface of the cap instead of the medicament delivery member cover and the groove can be provided on an external surface of the medicament delivery member cover. As a further example, the first shoulder does not have to have a groove but could be defined by a single shoulder structure; the groove could instead be provided in the internal surface of the housing.

The invention claimed is:

1. A medicament delivery device for injection of a medicament, comprising:
    a housing arranged to receive a medicament delivery member,
    a medicament delivery member cover received by the housing, which medicament delivery member cover has a cap-fitting portion,
    wherein the medicament delivery member cover is moveable relative to the housing from an extended position in which the cap-fitting portion extends from the housing, to a retracted position in which the medicament delivery member cover is biased towards the extended position, and
    a cap arranged to receive the cap-fitting portion,
    wherein the medicament delivery member cover and the cap comprises a tamper evidence mechanism which is activated by removal of the cap from the cap-fitting portion,
    wherein the tamper evidence mechanism comprises a groove and a first shoulder,
wherein first shoulder is arranged in the groove prior to removal of the cap,
    wherein the tamper evidence mechanism comprises a second shoulder arranged adjacent to the groove in the axial direction, and
    wherein the second shoulder has a first shoulder abutment surface arranged in an opposite direction relative to a second shoulder abutment surface of the first shoulder when the cap-fitting portion is received by the cap.

2. The medicament delivery device as claimed in claim 1, wherein the tamper evidence mechanism comprises a flexible tongue, wherein the first shoulder defines an end portion of the flexible tongue.

3. The medicament delivery device as claimed in claim 1, wherein the first shoulder increases in radial dimension along the axial direction, in that direction which enables release of the first shoulder from the groove by means of axial motion.

4. The medicament delivery device as claimed in claim 1, wherein the groove is defined by a surface which along the axial direction gradually increases in depth from its edge towards the midpoint of the groove.

5. The medicament delivery device as claimed in claim 1, wherein the second shoulder increases in radial dimension in the opposite direction relative to the direction along which the first shoulder increases in radial dimension.

6. The medicament delivery device as claimed in claim 1, wherein the groove is provided on an internal surface of the cap.

7. The medicament delivery device as claimed in claim 6, wherein the first shoulder is arranged on an external surface of the medicament delivery member cover.

8. The medicament delivery device as claimed in claim 6, wherein the groove extends along the inner periphery of the cap.

9. The medicament delivery device as claimed in claim 1, wherein the housing comprises a guide structure extending axially along an internal surface of the housing.

10. The medicament delivery device as claimed in claim 9, wherein the guide structure is arranged to cooperate with that part of the tamper evidence mechanism which is arranged on the medicament delivery member cover.

11. The medicament delivery device as claimed in claim 9, wherein the guide structure comprises a groove arranged to receive a first shoulder of the tamper evidence mechanism.

12. The medicament delivery device as claimed in claim 11, wherein the cap comprises a stop member.

13. The medicament delivery device as claimed in claim 12, wherein the stop member and the inner flange defines a play (P) for the proximal end flange of the medicament delivery member deshielder.

14. The medicament delivery device as claimed in claim 13, wherein the axial distance between the stop member and the inner flange is at least as large as the axial distance between the first shoulder abutment surface and a midpoint of the groove.

15. The medicament delivery device as claimed in claim 9, wherein the guide structure comprises a rib, wherein the first shoulder of the tamper evidence mechanism is arranged to receive the rib.

16. The medicament delivery device as claimed in claim 1, wherein the groove and the first shoulder define a snap fit.

17. The medicament delivery device as claimed in claim 1, comprising a medicament delivery member deshielder which comprises a proximal end flange,
    wherein the cap is arranged to receive the medicament delivery member deshielder.

18. The medicament delivery device as claimed in claim 17, wherein the cap comprises an inner flange arranged to cooperate with proximal end flange of the medicament delivery member deshielder.

* * * * *